(12) United States Patent
Wong

(10) Patent No.: US 8,260,410 B2
(45) Date of Patent: Sep. 4, 2012

(54) DEVICE FOR IDENTIFYING THE LIKELIHOOD OF A PATIENT SUFFERING A MYOCARDIAL INFARCTION

(76) Inventor: Yuk-ki Wong, Hamble (GB)

( * ) Notice: Subject to any disclaimer, the term of this patent is extended or adjusted under 35 U.S.C. 154(b) by 559 days.

(21) Appl. No.: 12/515,381

(22) PCT Filed: Nov. 16, 2007

(86) PCT No.: PCT/GB2007/004387
§ 371 (c)(1),
(2), (4) Date: May 18, 2009

(87) PCT Pub. No.: WO2008/059269
PCT Pub. Date: May 22, 2008

(65) Prior Publication Data
US 2010/0081951 A1   Apr. 1, 2010

(30) Foreign Application Priority Data
Nov. 18, 2006   (GB) .................................. 0623053.6

(51) Int. Cl.
*A61B 5/04* (2006.01)
(52) U.S. Cl. ....................................................... 600/519
(58) Field of Classification Search ................... 600/519, 600/481, 483, 484, 510, 509; 482/2, 5, 8; 340/539.12; 607/17, 44
See application file for complete search history.

(56) References Cited

U.S. PATENT DOCUMENTS

| 5,050,612 | A | * | 9/1991 | Matsumura | 600/483 |
| 6,021,350 | A | * | 2/2000 | Mathson | 607/17 |
| 6,021,650 | A | * | 2/2000 | Okuno et al. | 66/70 |
| 6,144,878 | A | | 11/2000 | Schroeppel | |
| 7,079,887 | B2 | * | 7/2006 | Burnes et al. | 600/510 |
| 2004/0039265 | A1 | | 2/2004 | Bardy | |
| 2008/0183082 | A1 | * | 7/2008 | Farringdon et al. | 600/481 |
| 2011/0270101 | A1 | * | 11/2011 | Fischell et al. | 600/509 |

FOREIGN PATENT DOCUMENTS

| EP | 1219236 A2 | 7/2002 |
| GB | 2397527 A | 7/2004 |
| WO | 03063684 A2 | 8/2003 |
| WO | 2005006969 A1 | 1/2005 |
| WO | 2006093712 A2 | 9/2006 |
| WO | 2007049306 A1 | 5/2007 |

OTHER PUBLICATIONS

UK IPO Search Report dated Aug. 30, 2007, issued in corresponding Application No. GB 0623053.6, filed Nov. 18, 2006.

* cited by examiner

*Primary Examiner* — George Manuel
*Assistant Examiner* — Robert Wieland
(74) *Attorney, Agent, or Firm* — Christensen O'Connor Johnson Kindness PLLC

(57) ABSTRACT

A device for identifying the likelihood of a patient suffering a myocardial infarction comprises a heart rate monitor operative to generate an output indicative of the current heart rate of the patient, and memory means for storing heart rate data indicative of a heart rate of the patient at which angina has previously occurred. Electronic control means is provided and is operative to analyze both the output from the heart rate monitor and the heart rate data stored on the memory according to an algorithm so as to identify a change in the current heart rate indicative of an increased likelihood of the patient suffering myocardial infarction.

24 Claims, 4 Drawing Sheets

DEVICE FOR IDENTIFYING THE LIKELIHOOD OF A PATIENT SUFFERING A MYOCARDIAL INFARCTION

BACKGROUND OF THE INVENTION

The present invention relates to a device for identifying the likelihood of a patient suffering a myocardial infarction and particularly but not exclusively relates to such a device for use by the patient.

In coronary heart disease, the blood and oxygen supply to the heart is reduced because of one or more constrictions in the coronary arteries. This means that the amount of work that the heart can do, also known as the cardiac output, is limited and when a patient over-exerts, angina (chest pain) is experienced.

Myocardial infarction occurs when a coronary artery becomes completely or almost completely blocked. Such blockage may occur instantly or over a period of hours to months. Corresponding to this increasing blockage and in the period leading up to the myocardial infarction, patients often experience angina at lower levels of exertion and even at rest. Since cardiac output is linearly related to heart rate, angina occurring at low heart rates can be indicative of myocardial infarction.

Monitoring systems for heart rate and other physiological parameters have been proposed in prior patent applications WO 03/063684 and WO 05/006969.

WO 03/063684 aims to monitor physiological parameters alone to predict when chronic symptoms occur. The assumption is that when symptoms are stable, they usually occur under similar circumstances. However, such monitoring does not cope with unstable and unpredictable symptoms. In fact, if a symptom such as angina occurred outside of a predictive model, WO 03/063684 assumes that the model was wrong and a new model is reconstructed instead of an alert for instability being issued.

WO 05/006969 also aims to monitor physiological parameters with the aim of predicting disease states. However, physiological parameters are not specifically sampled at times of symptoms and analysis does not take into account whether patients were symptomatic at the time of sampling.

Another patent application, US 006144878A, proposes evaluation of heart rate variability to forecast a cardiac event. Heart rate variability is a specific medical term that is used in this document to refer to the beat-to-beat variation in heart rate, rather than to different heart rates at different exertion levels or to the different heart rates at which angina may occur.

If patients could identify an increased likelihood of myocardial infarction during the pre-infarction stage, treatment could be given to prevent the myocardial infarction. Such treatments include, for example, anti-platelet agents such as Clopidogrel®, and/or interventions such as coronary bypass surgery and percutaneous coronary intervention.

BRIEF SUMMARY OF THE INVENTION

According to a first aspect of the invention there is provided a device for identifying the likelihood of a patient suffering a myocardial infarction, the device comprising a heart rate monitor operative to generate an output indicative of the current heart rate of the patient, memory means for storing heart rate data indicative of a heart rate of the patient at which angina has previously occurred, and electronic control means operative to analyse both the output from the heart rate monitor and the heart rate data stored on the memory according to an algorithm so as to identify a change in the current heart rate indicative of an increased likelihood of the patient suffering myocardial infarction.

Preferably the memory means and the electronic control means are integral with the heart rate monitor.

Preferably the device is operative to generate a warning signal when a change in the current heart rate is identified that is indicative of an increased likelihood of the patient suffering myocardial infarction.

Preferably the electronic control means analyses heart rate data indicative of the patient's symptomatic heart rate, that is, the heart rate at which angina has previously occurred in that patient, the device generating the warning signal when the current heart rate falls below the symptomatic heart rate.

Preferably the device generates a warning signal when the current symptomatic heart rate falls below the symptomatic heart rate.

Preferably input means are provided to enable the patient to send a datum signal to the electronic control means indicative that the patient is currently suffering from angina, the datum signal being stored on the memory means together with data indicative of the patient's heart rate at the time of the datum signal, so as to comprise the heart rate data.

Alternatively or additionally the electronic control means analyses heart rate data indicative of the patient's background heart rate, that is, the heart rate of the patient when not suffering from angina, the device generating the warning signal when the current heart rate falls below or rises above relative to the background heart rate.

Preferably the electronic control means is operative to analyse the output from the heart rate monitor and the heart rate data stored on the memory according to an algorithm so as to detect an adverse trend in the background heart rate of the patient.

Preferably the device comprises display means operative to display information to the patient.

Preferably the electronic control means is operative to display a signal on the display means indicative of an increased likelihood of the patient suffering a myocardial infarction, when such an increased likelihood is identified by the electronic control means.

Preferably the electronic control means is operative to display a signal on the display means indicative that the patient should monitor his heart rate more frequently.

Preferably the heart rate monitor comprises sensor means adapted to be in contact with the patient's body.

The sensor means may be adapted to be in contact with the patient's body at the control of the patient.

The sensor means may be adapted to be in contact with the patient's body continuously, the heart rate monitor being operative to automatically monitor the patient's heart rate at predetermined intervals.

Preferably, the device further comprises data transfer means operative to enable the device to connect to other devices so as to enable data transfer between devices. Such other devices may measure a physiological variable selected from the group of variables including blood pressure, peak flow rate, blood sugar and patient weight.

The data transfer means may be adapted to enable the devices to be connected wirelessly.

The data transfer means is preferably operative to enable data to be output to an external device such as a printer, a computer or the internet.

Preferably, the memory means is operative to store data in a standardised form comprising a series of related fields, the fields including at least the following:
1. Description of data;
2. Value of data; and
3. Date and time stamp of data entry;

Preferably the standardized form includes at least one of the following further fields:
4. Source of data; and
5. Privacy indicator.

Field 1 describes the data, such as heart rate for example, whilst Field 2 stores the actual value of the heart rate. Field 4 stores, for example, the serial number of a device. Field 5 indicates whether the data is accessible to all users of the device or whether the data should have restricted access.

Some data is meaningless on its own. For instance, the heart rate should be recorded together with information as to whether angina occurred. Preferably the standardized form includes a further field comprising a common index identifying data that should be considered together.

A variety of different algorithms may be used to detect changes in the symptomatic heart rate. For example, the algorithm may detect when the symptomatic heart rate drops below a predetermined threshold.

Alternatively, the algorithm may use a technique such as statistical process control to detect an adverse trend in heart rate even though the symptomatic heart rate has not yet dropped below the predetermined threshold. When such an adverse trend is detected, the electronic control means preferably sends a signal to the patient indicative that more frequent measurements of the patient's heart rate should be obtained.

The electronic control means may be operative according to a plurality of algorithms, at least one of the algorithms being operative to identify a change in the background heart rate.

The electronic control means may comprise a further algorithm to analyse a physiological variable selected from the group comprising patient weight, blood sugar, blood pressure and peak flow rate.

Preferably, the electronic control means comprises a microprocessor that runs a program which, in use, implements the predetermined algorithm or algorithms. Preferably the algorithm or algorithms can be added to or removed from the electronic control means.

Other aspects of the present invention may include any combination of the features or limitations referred to herein.

BRIEF DESCRIPTION OF THE SEVERAL VIEWS OF THE DRAWINGS

The present invention may be carried into practice in various ways, but embodiments will now be described by way of example only with reference to the accompanying drawings in which.

DETAILED DESCRIPTION OF THE INVENTION

Figure 1:
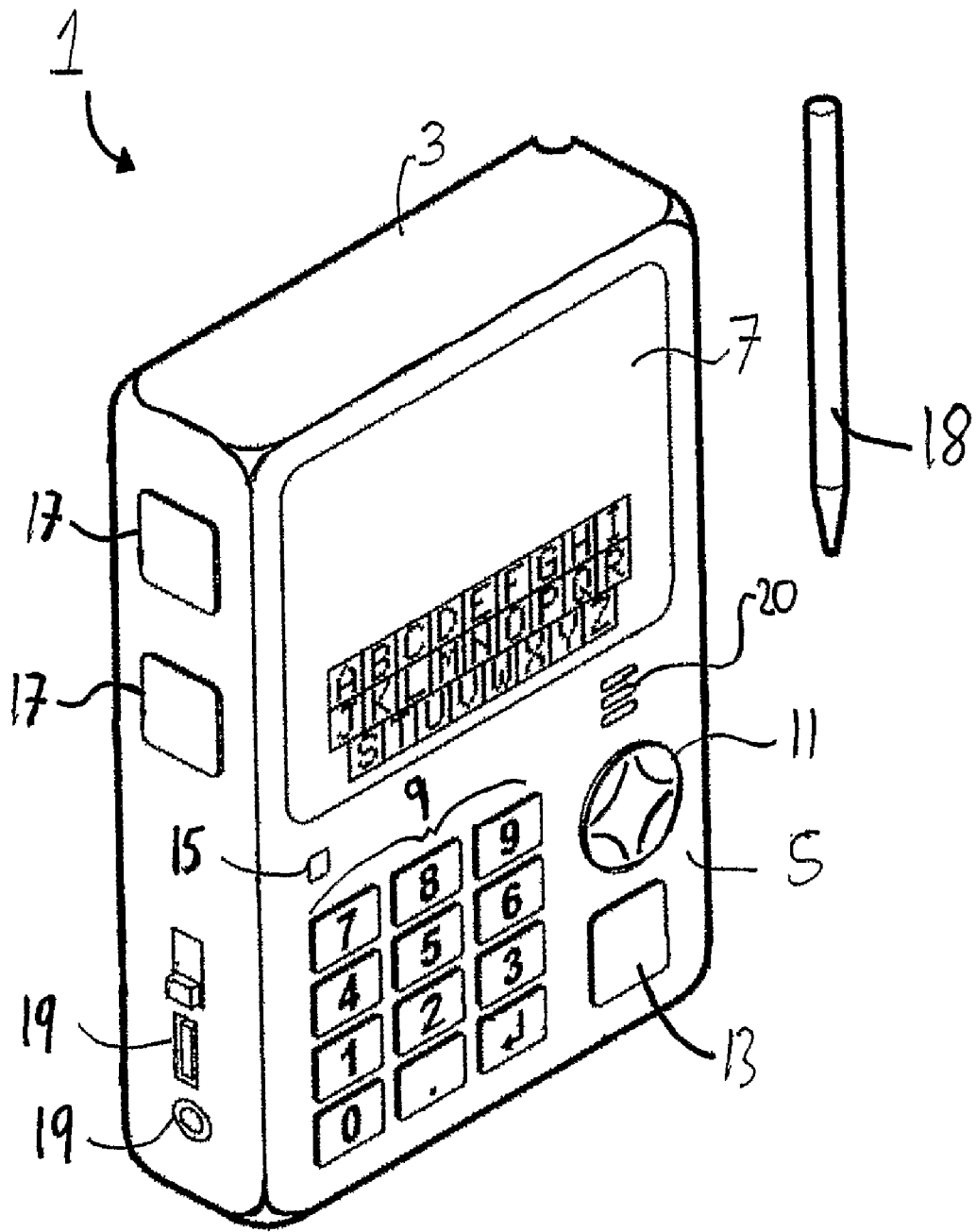
FIG. 1 is a perspective view from the front of a first device in accordance with the present invention.
Figure 2:
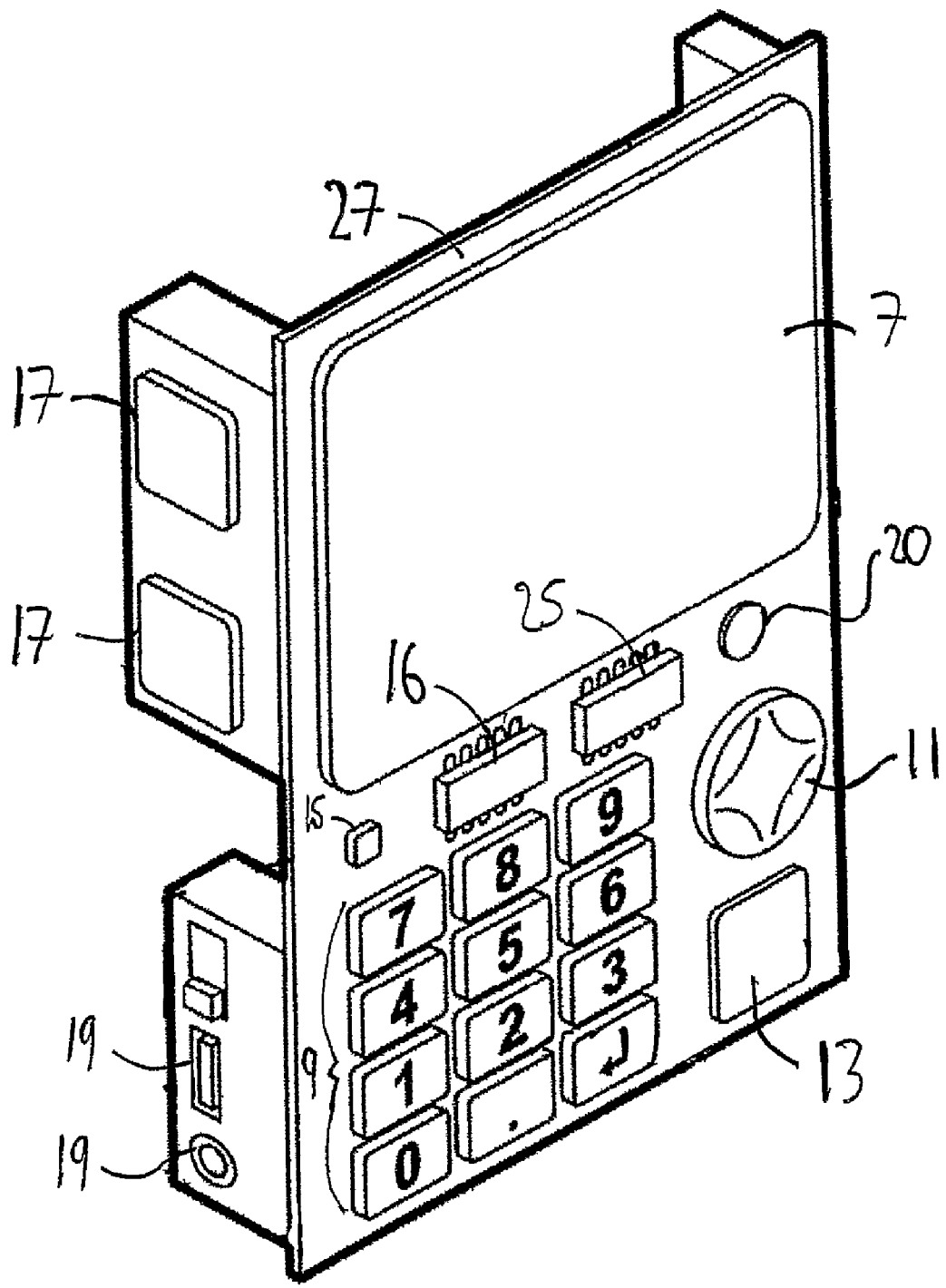
FIG. 2 is a perspective view of the device of FIG. 1 with part of the device removed for clarity.
Figure 3:
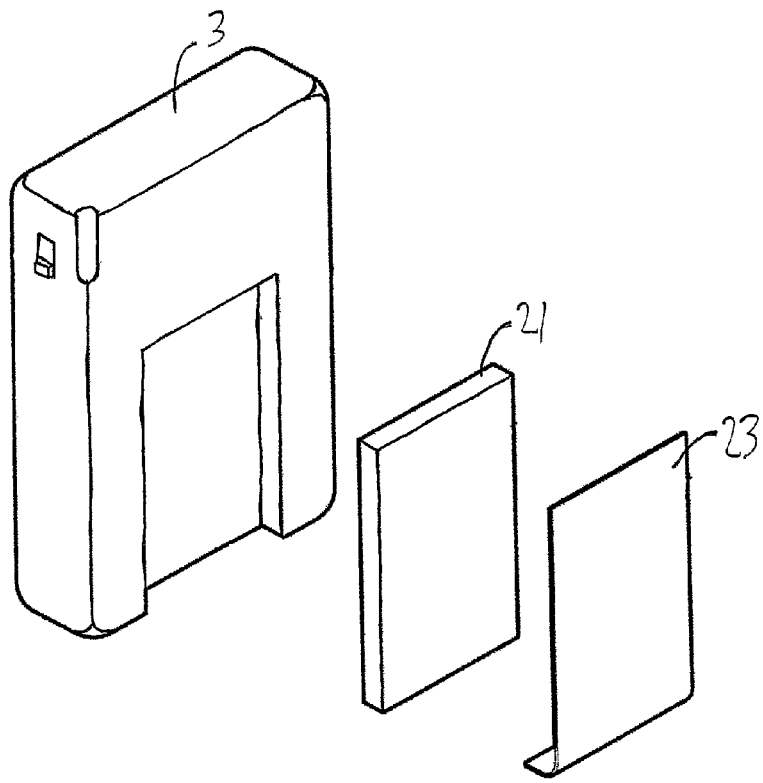
FIG. 3 is a perspective exploded view from the rear of the device of FIGS. 1 and 2.

The first device 1 of FIGS. 1 to 3 incorporates a heart rate monitor that is not in continuous contact with the user. The second device 31 of FIGS. 4 to 6 incorporates a heart rate monitor that in use of the device is in constant contact with the user's skin. The third device 51 of FIG. 7 incorporates a heart rate monitor that can be surgically implanted beneath the patient's skin so as to be in continuous contact with the patient's body. A heart rate monitor is used because heart rate is a surrogate marker for a patient's cardiac output.

Referring initially to FIGS. 1 to 3, the first device 1 comprises an oblong case 3 the front panel 5 of which is provided with an LCD display 7, a numeric keypad 9, a joystick type keypad 11, and a button 13 operative to enable the patient to send a signal to the device 1 indicating that the patient is currently suffering from angina. The front panel 5 is also formed with a warning means comprising a LED 15 and a speaker 20. In this example, the LCD display 7 is a touch screen display and is provided with a stylus 18 to input data to the device 1 by touching the stylus 18 to the display 7.

The display 7 is controlled by electronic control means to display, for example, the current time and date, the remaining power of the battery, and information about the current or historical heart rate of the patient, and the heart rate at which angina occurs. This displayed information could also include suggested frequency and timing of when the patient should measure heart rate, and preferably other physiological variables. The electronic display 7 could also be used to display a touch keyboard so that the patient can enter data to the device 1 such as a password or their name for example.

The numeric keypad 9 can be used by the patient to enter data to the device 1, the data, for example, relating to physiological variables such as weight, peak flow rate, blood sugar and blood pressure as such variables are numeric in type. As another example, the numeric keypad 9 may be used for entering a PIN number, to enable the patient to use the device 1.

The button 13 is operative to send an electrical signal to the electronic control means indicating that the patient is suffering from angina at the time the button 13 is pressed. To prevent erroneous data from accidental operation, the button 13 may be mounted flush with the surface of the case 3.

The device 1 further comprises a heart rate monitor comprising a control chip 16 connected to sensor means comprising two spaced apart finger pads that are electrical contacts 17 on the side of the case 3.

The side of the case 3 is also provided with date transfer means in the form of data jacks 19. Data may therefore be input to the device 1 from, for example, a weighing device, a blood pressure measuring device or a blood sugar measuring device. The data transfer means may comprise a Universal Serial Bus port, a wireless connection or a Bluetooth® connection.

The rear of the case 3 stores a battery 21 that powers the device and which is retained by a removable cover 23.

The electronic control means comprises electronic circuitry that includes an IC chip 25 mounted on a circuit board 27, the IC chip 25 being connected to the heart rate monitoring control chip 16.

The IC chip 25 includes the following components:
a microprocessor for controlling the operation of the device 1;
a non-volatile read-only memory for storing a control program for execution by the microprocessor, the control program being operative according to at least one algorithm;
a non-volatile re-writable memory for storing heart rate data obtained from the heart rate monitor, other physiological data obtained from external devices, and data used by the control program to run the algorithm(s) and control the display 7;
random access memory used by the microprocessor; and
an internal clock.

The two memories of the IC chip 25 may be constituted by different regions of the same memory element, for example an EPROM. Any suitable architecture for the IC chip 25 may be used. As an alternative, it would be possible to provide the various components of the IC chip 25 in separate IC chips.

When the device is activated the heart rate monitor generates an output comprising a current heart rate signal that is sent to the microprocessor when the patient presses his fingertips to the electrical contacts 17. The current heart rate signal consists of a description of the data which in this case is 'heart rate', the value of the data which in this case is the number of heart beats per minute, the source of the data which in this case is the integral heart rate monitor, and a number that is used for indexing. On receipt of such a signal, the microprocessor stores this data on the non-volatile rewritable memory together with the time and date as derived using the internal clock.

The microprocessor then controls the electronic display 7 to show a message requesting the user to indicate by pressing the button 13 whether or not they are currently experiencing angina.

If the button 13 is pressed, a further signal is sent to the microprocessor which consists of a description of the data which in this case is 'angina' the value of the data which in this case is 'yes', the source of the data which in this case is a code identifying button 13, and a number that is used for indexing which in this case is the same as the corresponding index number for the associated heart rate data.

The data from this second signal is also stored on the rewritable memory by the microprocessor. If the button 13 is not pressed within a predetermined period, for example ten seconds, the microprocessor would store data for 'angina' which includes a value of 'no'.

The microprocessor subsequently analyses the heart rate data stored in the memory according to the control program which implements at least one predetermined heart rate change algorithm.

The heart rate change algorithm is operative to enable the microprocessor to detect either a fall in the patient's symptomatic heart rate (the heart rate of the patient measured when suffering from angina) and/or rise or fall in the background heart rate (heart rate measured when the patient does not have angina), below or above a predetermined heart rate that is indicative of an increased risk of the patient suffering a myocardial infarction.

The control program also implements a predetermined heart rate trend algorithm that is operative to enable the microprocessor to detect an adverse trend in the patient's background heart rate when the background heart rate is not above or below the predetermined level indicative of an increased risk of myocardial infarction. Suitable algorithms will be described in more detail below.

On detecting a heart rate above or below the predetermined level indicative of an increased risk of a myocardial infarction, the microprocessor causes the LED 15 and/or speaker 20 to output a warning to the user. This warning signifies that the patient should consult a doctor to consider the possibility of preventative treatment. The microprocessor also records the time and date of each warning in the rewritable memory. A warning signal may also be provided to the patient via the display 7, or via an external device connected to one of the data jacks 19. A decrease in the background heart rate can be significant because it can be indicative of the patient restricting their physical activity because angina is occurring at lower exertion levels. An increase in background heart rate can be significant because there can be a higher risk that the symptomatic heart rate may be exceeded.

On detecting an adverse trend in the background heart rate, the microprocessor outputs a message on the electronic display 7 indicating that an increased frequency of heart rate monitoring by the patient is required. The message may indicate a suggested monitoring frequency. This message signifies that an increased frequency of monitoring may detect an increased likelihood of a myocardial infarction at an earlier stage.

Patients with co-morbid disease(s) may also use external devices to measure physiological variables other than heart rate. For example, a patient with heart failure may use a weighing machine to measure weight. Activation of a compatible weighing machine causes an electrical signal indicative of the weight of the patient to be sent to the microprocessor of the device 1 via the data transfer means. In this case, the description of the data in such a signal would be 'weight', the value of the data would be the weight in kilograms, and the source of the data could be a serial number identifying the weighing machine.

Alternatively, the weight data could be entered manually via the electronic display 7 or numeric keypad 9 and the electrical signal sent to the microprocessor would then indicate that the source of the data was either the electronic display 7 or numeric keypad 9 respectively.

Data for physiological variables other than heart rate is analysed by the microprocessor in a similar manner to that for heart rate in order to detect an increased risk of deterioration of a co-morbid disease associated with that physiological variable, or for detecting adverse trends that may indicate an increased likelihood that a co-morbid disease is likely to occur. Similarly, detection of an increased likelihood will cause a warning signal to be output to the patient, and detection of an adverse trend would cause the display of a message on the display 7 suggesting an increased frequency of measurement of the physiological variable.

The algorithms used to detect an increased likelihood of a myocardial infarction will now be described. In general, any algorithm which identifies a clinically important increase may be used. There is considerable flexibility in the choice of algorithms. For example, it might be desirable to vary the predetermined heart rate at which a warning is output to the patient.

A preferred heart rate change algorithm based on the heart rate at which angina usually occurs is as follows:

For the purposes of defining the heart rate change algorithm, the symptomatic heart rate, that is the heart rate of the patient at which angina occurs, is determined during an initial calibration of the device 1. Preferably, a standardised treadmill exercise test known as the 'Bruce Protocol' is carried out under medical supervision. The heart rate at which angina occurs during the exercise test, or the maximal heart rate achieved if the user does not experience angina, is taken to be the symptomatic heart rate. This symptomatic heart rate is entered into and stored on the electronic control means of the device 1.

Alternatively, if an exercise test cannot be carried out, the device 1 may be operated by the patient initially in a calibration mode during which the mean heart rate at which angina occurs at a plurality of different times is taken to be the symptomatic heart rate. This may be achieved by the patient pressing the button 13 when suffering from angina. Any number of angina episodes may be used for calibration, but preferably one to three episodes would be used. If a myocardial infarction occurs within the calibration period, the device 1 is reset and recalibrated.

The heart rate change algorithm controls the microprocessor to generate a warning should angina occur at a heart rate that is a predetermined amount lower than the symptomatic heart rate, typically 8 to 20% lower although any other desired predetermined amount could alternatively be used.

A preferred heart rate change algorithm operative to use the background heart rate is determined as follows:

The patient is initially required to perform a certain amount of exertion on a daily basis. Preferably, the same exertion is carried out at the same time every day and could include, for example, climbing a flight of stairs. The device 1 is used to measure the heart rate of the patient after exertion has been completed and this heart rate is taken to be the background heart rate. This heart rate data is entered on to the device 1 and is stored on the rewritable memory of the IC chip 25.

The heart rate change algorithm is operative to enable the micro processor to generate a warning signal via the LED, speaker 20 or display 7 to the patient should the heart rate either fall below a predetermined level, typically 10 to 20% of the background heart rate, or rise above a predetermined level, typically 10 to 20% of the background heart rate.

A heart rate trend algorithm operative to use adverse trends in the symptomatic or background heart rate is as follows:

Sequential measurements of the symptomatic or background heart rate (obtained as described above) are analysed by statistical process control methods such as control charts. Typically, five or more heart rate measurements are analysed.

In the case of the symptomatic heart rate, the heart rate trend algorithm is operative to enable the microprocessor to generate a warning signal should the symptomatic heart rate fall over time.

In the case of the background heart rate, the heart rate trend algorithm is operative to enable the microprocessor to generate a warning should the background heart rate fall or rise over time.

The algorithm used to detect an increased likelihood of deterioration of a co-morbid chronic disease will now be described. In general, any algorithm which identifies a clinically important increase may be used.

Preferably, one or more physiological variables are chosen to monitor each co-morbid disease. For example, weight is used to monitor heart failure and blood sugar is used to monitor diabetes. Preferably, for each physiological variable, an optimum value with upper and lower limits will be determined by the supervising physician and inputted to the device 1 when in a calibration mode. In some cases, no upper limit need be defined, as is the case for the peak flow rate. In some cases, a derivative of the variable may be used for monitoring. For example, the ratio of the peak flow rate at 18:00 h to the peak flow rate at 09:00 h may be used to monitor chronic obstructive airways disease.

The algorithm is operative to enable the microprocessor to generate a warning signal should a variable or its derivative exceed its predetermined upper limit or fall below its predetermined lower limit.

Figure 4:
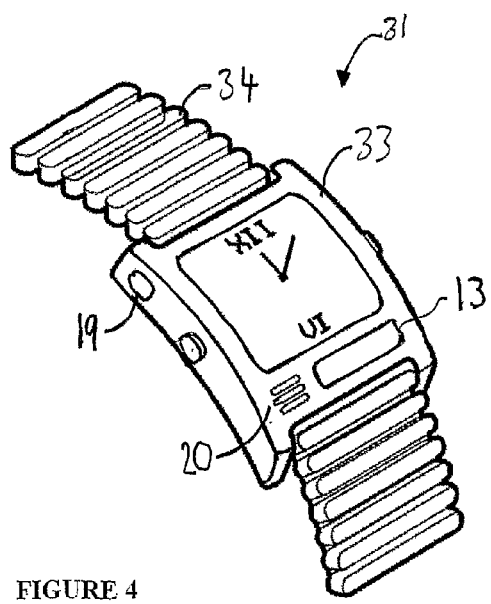
FIG. 4 is a perspective view from the front of a second device in accordance with the present invention.
Figure 5:
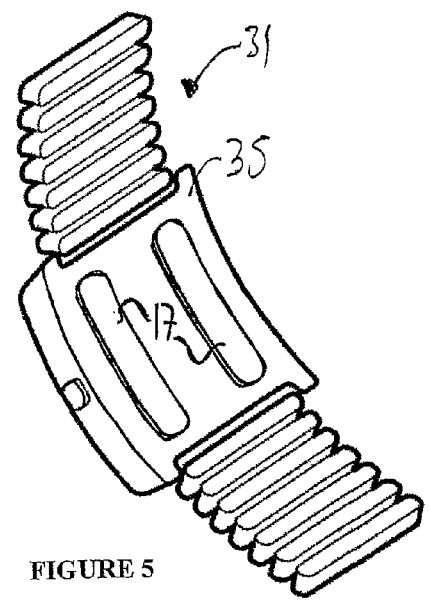
FIG. 5 is a perspective view from the underside of the device of FIG. 4.
Figure 6:
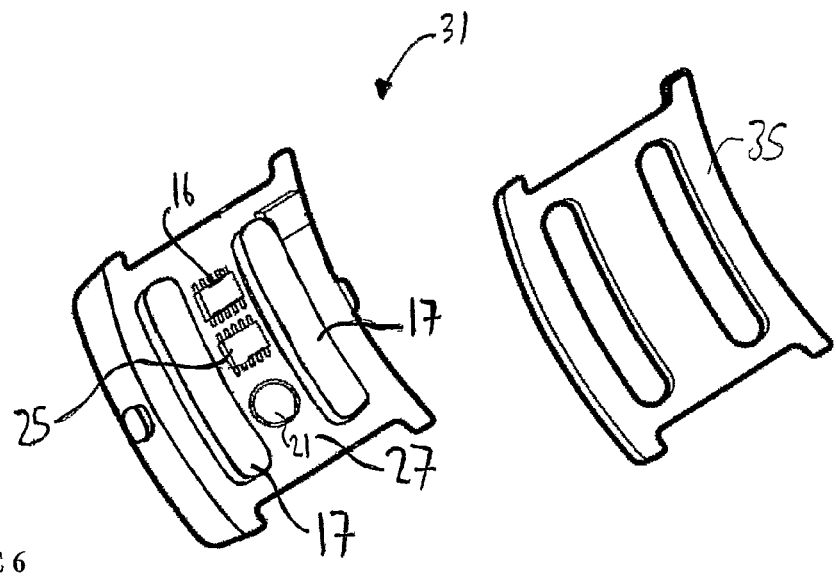
FIG. 6 is an exploded perspective view from the underside of the device of FIGS. 4 and 5 with part of the device removed for clarity.

Referring now to FIGS. 4 to 6, a second device 31 includes many components and an electronic control means identical to those of the first device 1. Common components are referenced using the same reference numerals.

The second device 31 is adapted to be worn on the wrist of the patient and comprises a case 33 which has a flexible wrist strap 34 arranged so that the case 33 can be held firmly against the wrist of the user. The case 33 has a compartment accommodating the chip 16 of the heart rate monitor and the electronic control means as described above, and a rear panel 35 which closes off the compartment.

In this device 31, the two electrical contacts 17 are arranged to protrude through the rear panel 35 so that when the device 31 is worn on the patient's wrist the contacts 17 are in constant contact with the patient's wrist.

The second device 31 in this example has only one data jack 19 that is used for data input and output, it does not have the numeric keypad 9, and the electronic display 7 is not touch operated.

The operation of the electronic control means tinder the control of the control program running in the microprocessor of the second device 31 is the same as that for the first device 1 with the following differences:

The heart rate of the user is sampled automatically at frequent intervals, typically five to ten minutes, in order to calculate the patient's background heart rate. Operation of button 13 sends a signal to the microprocessor indicating that the user is experiencing angina. The microprocessor is then operative to sample the patient's heart rate. The data from the signal from button 13, and the corresponding data from the signal from the electrical contacts 17 are stored on the rewritable memory of the device 31 with the same index number. To prevent erroneous data from accidental operation of button, one possible arrangement would be for button 13 to be mounted flush with the surface of case 33.

In the second device 31, the heart rate is sampled at frequent and regular intervals and the mean heart rate is taken to be the background heart rate, background heart rates for the day and for the night being determined. Typically, the day background rate would be measured between 09:00 h and 23:00 h and the night background rate would be measured during the remaining period.

By measuring the background heart rate automatically and frequently, the second device 31 may automatically detect an increased risk of myocardial infarction relatively early.

Figure 7:
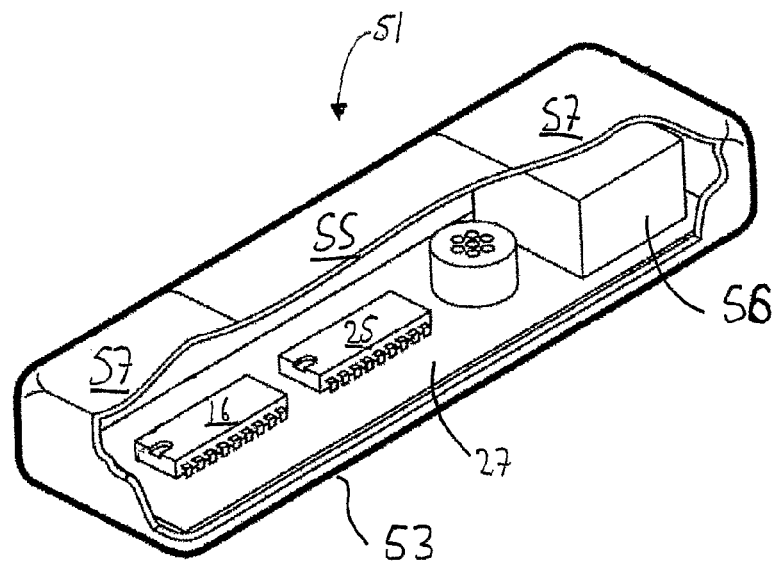
FIG. 7 is a perspective view of a third device in accordance with the present invention with part of the device removed for clarity.

Referring to FIG. 7, the third device 51 is designed to be used in conjunction with the first device 1 and functions as an external heart rate monitor for the first device 1. Parts of the third device 51, including the electronic circuitry, are identical to the first device 1 and the same reference numerals will therefore be used.

The third device 51 comprises a case 53 that encloses a compartment containing the electronic control means. In use, the case 53 is implanted under the skin of the left side of the chest of the patient and consists of electrodes 57 separated by non-conductive material 55. The IC chip 25, a battery 56, the microprocessor and wireless communication means for input and output of data are all mounted within the case 53.

In use of the third device 51, the heart rate of the user is sampled automatically at frequent intervals, typically five to ten minutes, in order to calculate the background heart rate. This background heart rate data is stored in the rewritable memory of the third device 51 and, when the third device 51 is in wireless communication with the first device 1, all data is downloaded to the first device 1 via the wireless terminals of both devices 1, 51.

When the first device 1 is used in conjunction with the third device 51 and when the first device 1 is in wireless communication with the third device 51, all heart rate data including background heart rate data is obtained from the third device 51 rather than from the first device 1 but otherwise, the operation of the first device 1 is unchanged.

As the third device 51 is implanted under the skin, there is more certainty that the patient's background heart rate will be measured frequently and automatically.

The control program of the first device 1 could reside in the microprocessor of any commercially available mobile telephone and the data from any commercially available heart rate monitor could be inputted into said program.

Whilst the devices 1, 31 and 51 have been described as measuring heart rate by detecting the electrocardiogram signal, other means for measuring heart rate could alternatively be used, including, for example, pulse oximetry or electronic stethoscopes.

When stable, some patients do not get angina. Nevertheless, it is possible to determine their background heart rate for exertion levels such as maximal exercise on a treadmill or minimal exercise after walking a short distance on the flat. Subsequently, if angina does occur, it is more likely to indicate an impending myocardial infarction if it occurs at heart rates near to that for minimal exercise. Therefore, by monitoring each episode of angina and measuring the corresponding heart rate, it is possible to determine when angina is becoming unstable and thus obtain early warning for an impending myocardial infarction. Monitoring heart rate alone is not sufficient. Low heart rate is universal during sleep and common throughout the day at rest. In such situations, this does not mean that a patient will have a myocardial infarction unless they are also experiencing angina.

The devices 1, 31 & 51 may also be operative to output a warning to the user if the user experiences angina at a level of exertion equivalent to walking two to three blocks, when previously they had experienced angina at a higher level of exertion. This test is as issued by the American College of Cardiology and the American Heart Association Guidelines for the Management of Patients with Unstable Angina/Non-St Elevation Myocardial Infarction.

The invention claimed is:

1. A device for identifying the likelihood of a patient suffering a myocardial infarction, the device comprising a heart rate monitor operative to generate an output indicative of the current heart rate of the patient, memory means for storing heart rate data indicative of a heart rate of the patient at which the patient has previously experienced angina, and electronic control means for determining a likelihood of the patient suffering myocardial infarction, said electronic control means including means for analyzing the output from the heart rate monitor indicative of the patient's current heart rate and the heart rate data stored in the memory means indicative of a heart rate at which the patient previously experienced angina according to an algorithm based on the patient's heart rate to identify a change in the current heart rate and indicate a likelihood of the patient suffering myocardial infarction.

2. The device of claim 1 wherein the memory means and the electronic control means are integral with the heart rate monitor.

3. The device of claim 1 wherein the device is operative to generate a warning signal when a change in the current heart rate is identified that is indicative of an increased likelihood of the patient suffering myocardial infarction.

4. The device of claim 3 wherein the electronic control means analyses heart rate data indicative of the patient's symptomatic heart rate, that is, the heart rate at which angina has previously occurred in that patient, the device generating the warning signal when the current heart rate falls below the symptomatic heart rate.

5. The device of claim 1 wherein input means are provided to enable the patient to send a datum signal to the electronic control means indicative that the patient is currently suffering from angina, the datum signal being stored on the memory means together with data indicative of the patient's heart rate at the time of the datum signal, so as to comprise the heart rate data.

6. The device of claim 1 wherein the electronic control means analyses heart rate data indicative of the patient's background heart rate, that is, the heart rate of the patient when not suffering from angina, the device generating the warning signal when the current heart rate falls below or rises above relative to the background heart rate.

7. The device of claim 1 wherein the electronic control means is operative to analyse the output from the heart rate monitor and the heart rate data stored on the memory according to an algorithm so as to detect an adverse trend in the background heart rate of the patient.

8. The device of claim 1 wherein the device comprises display means operative to display information to the patient.

9. The device of claim 8 wherein the electronic control means is operative to display a signal on the display means indicative of an increased likelihood of the patient suffering a myocardial infarction, when such an increased likelihood is identified by the electronic control means.

10. The device of claim 8 wherein the electronic control means is operative to display a signal on the display means indicative that the patient should monitor his heart rate more frequently.

11. The device of claim 1 wherein the heart rate monitor comprises sensor means adapted to be in contact with the patient's body.

12. The device of claim 11 wherein the sensor means is adapted to be in contact with the patient's body at the control of the patient.

13. The device of claim 11 wherein the sensor means is adapted to be in contact with the patient's body continuously, the heart rate monitor being operative to automatically monitor the patient's heart rate at predetermined intervals.

14. The device of claim 1 wherein the device further comprises data transfer means operative to enable the device to connect to other devices so as to enable data transfer between devices.

15. The device of claim 14 wherein the data transfer means is adapted to enable the devices to be connected wirelessly.

16. The device of claim 14 wherein the data transfer means is operative to enable data to be output to an external device such as a printer, a computer or the Internet.

17. The device of claim 1 wherein the memory means is operative to store data in a standardised form comprising a series of related fields, the fields including at least the following:
1. Description of data;
2. Value of data; and
3. Date and time stamp of data entry.

18. The device of claim 17 wherein the standardized form includes at least one of the following further fields:
4. Source of data; and
5. Privacy indicator.

19. The device of claim 17 wherein the standardized form includes a further field comprising a common index identifying data that should be considered together.

20. The device of claim 1 wherein the electronic control means is operative according to a plurality of algorithms, at least one of the algorithms being operative to identify a change in the background heart rate.

21. The device of claim 20 wherein the electronic control means comprises a Further algorithm to analyse a physiological variable selected from the group comprising patient weight, blood sugar, blood pressure and peak flow rate.

22. The device of claim 20 wherein the electronic control means comprises a microprocessor that runs a program which, in use, implements the predetermined algorithm or algorithms.

23. The device of claim 20 wherein the algorithm or algorithms can be added to or removed from the electronic control means.

24. A device for identifying the likelihood of a patient suffering a myocardial infarction, the device comprising a heart rate monitor operative to generate an output indicative of a current heart rate trend of the patient, memory means for storing heart rate trend data indicative of a heart rate trend of the patient at which the patient has previously experienced angina, and electronic control means for determining a likelihood of the patient suffering myocardial infarction, said electronic control means including means for analyzing the output from the heart rate monitor indicative of the patient's current heart rate trend and the heart rate trend data stored in the memory means indicative of a heart rate trend at which the patient previously experienced angina according to an algorithm based on the patient's heart rate to identify a change in the current heart rate trend and indicate a likelihood of the patient suffering myocardial infarction.

* * * * *